United States Patent
Maljkovic et al.

(10) Patent No.: US 8,119,764 B2
(45) Date of Patent: *Feb. 21, 2012

(54) MEDICAL DEVICES MADE OF A POLYMER MATERIAL

(75) Inventors: Nikica Maljkovic, New Orleans, LA (US); Bianca Sadicoff Shemper, Hattiesburg, MI (US); Mohammad Jamal El-Hibri, Atlanta, GA (US)

(73) Assignee: Solvay Advanced Polymers, L.L.C., Alpharetta, GA (US)

( * ) Notice: Subject to any disclaimer, the term of this patent is extended or adjusted under 35 U.S.C. 154(b) by 613 days.

This patent is subject to a terminal disclaimer.

(21) Appl. No.: 12/206,825

(22) Filed: Sep. 9, 2008

(65) Prior Publication Data

US 2009/0082539 A1 Mar. 26, 2009

Related U.S. Application Data

(60) Provisional application No. 60/971,314, filed on Sep. 11, 2007, provisional application No. 60/971,934, filed on Sep. 13, 2007, provisional application No. 60/981,874, filed on Oct. 23, 2007, provisional application No. 60/982,193, filed on Oct. 24, 2007.

(51) Int. Cl.
*C08G 16/00* (2006.01)
*C08G 16/06* (2006.01)
*C08F 283/00* (2006.01)
*C08F 283/08* (2006.01)

(52) U.S. Cl. ........ 528/396; 528/220; 528/127; 528/128; 264/45.9; 264/319; 525/534; 424/9.322

(58) Field of Classification Search .................. 528/396, 528/220, 127, 128; 525/534; 424/9.322; 264/45.9, 319

See application file for complete search history.

(56) References Cited

U.S. PATENT DOCUMENTS

| 7,268,193 | B2 | 9/2007 | Marrocco, III et al. |
| 7,750,091 | B2 | 7/2010 | Maljkovic et al. |
| 7,875,696 | B2 * | 1/2011 | Myrick et al. ................ 528/127 |

FOREIGN PATENT DOCUMENTS

| WO | WO02072007 A2 | 9/2002 |
| WO | W02004004592 A1 | 1/2004 |
| WO | W02005102406 A1 | 11/2005 |
| WO | W02006008739 A2 | 1/2006 |
| WO | W02006037078 A2 | 4/2006 |
| WO | WO 2007/101845 | 9/2007 |

OTHER PUBLICATIONS

Dijckstra D.J. et al., "Worm-like morphology of semi-rigid substituted poly(p-phenylene)", J. Material Science, 2007, vol. 42, p. 3810-3815, DOI 10.1007/s10853-006-0426-8, Ed. Springer Science+Business Media, LLC ; 6 pgs.

Schwartz M., "Collaborative research and development (CT&D) Delivery order 0023: Molecular simulation for material design limits", Nov. 2005 ; 59 pg.

U.S. Appl. No. 12/719,181, Satchit Srinivasan et al., filed Mar. 8, 2010.

U.S. Appl. No. 12/676,989, David B. Thomas et al., Apr. 21, 2010.

U.S. Appl. No. 12/764,684, Mohammad J. El-Hibri et al., Apr. 21, 2010.

Orgando J., "Unreinforced plastics get stiffer", Design news (Nov. 6, 2006), vol. 61, (16), p. 57 (3 p.).

Solvay Advanced Polymers, "More remarkable PrimoSpire™ self-reinforced polyphenylene", Brochure PR-50497—accessible online from Solvay Advanced Polymers website since Oct. 2006—retrieved on Sep. 3, 2008 via http://www.solvayadvancedpolymers.com/static/wma/pdf/8/7/5/7/more_remarkable_PrimoSpire.pdf (4 p.).

* cited by examiner

*Primary Examiner* — Duc Truong

(74) *Attorney, Agent, or Firm* — Oblon, Spivak, McClelland, Maier & Neustadt, L.L.P.

(57) ABSTRACT

Medical device (Δ) comprising at least one part (π) consisting of a polymer material (M) comprising at least one kinked rigid-rod polyarylene (P) of which more than 50 wt. % of the recurring units are recurring units (R) of one or more formulae consisting of an optionally substituted arylene group which is linked by each of its two ends to two other optionally substituted arylene groups via a direct C—C linkage. The recurring units (R) are a mix (μ) consisting of (i) between 0 and 75 mole %, of rigid rod-forming arylene units (Ra) and (ii) between 25 and 100 mole % of kink-forming arylene units (Rb), both contents being based on the total number of moles of the recurring units (R). Arylene units (Ra) and/or (Rb) may be optionally substituted by at least one monovalent substituting group.

26 Claims, No Drawings

MEDICAL DEVICES MADE OF A POLYMER MATERIAL

REFERENCE TO RELATED APPLICATIONS

This application claims priority to and benefit under 35 U.S.C. §119(e) to U.S. provisional application No. 60/982,193 filed Oct. 24, 2007, to U.S. provisional application No. 60/981,874 filed Oct. 23, 2007, to U.S. provisional application No. 60/971,934 filed Sep. 13, 2007, and to U.S. provisional application No. 60/971,314 filed Sep. 11, 2007, the whole content of these applications being incorporated herein by reference for all purposes.

FIELD OF THE INVENTION

The present invention relates to medical devices made of a particular polymer material.

BACKGROUND OF THE INVENTION

Medical devices should be here understood under their broadest meaning, i.e. devices useful for the prevention, cure, alleviation, or correction of diseases, injuries, irregularities, disorders and deformities of any part of a human or animal body. They include not only devices useful for the prevention, cure or alleviation of diseases by non operative procedures, but also surgical devices (i.e. devices which treat diseases or injury by operative procedures), dental devices (i.e. devices useful for the prevention, cure or alleviation of diseases of the teeth, orthodontic devices (i.e. devices useful for the prevention or correction of irregularities of the teeth) and orthopedic devices (i.e. devices useful for disorders or deformities of the spine and joints) and the like.

Medical devices are made from a variety of materials, such as metal and polymers. They are generally sterilized. Because of their functionality, they need generally to have a complex design.

Parts of medical devices having very complex shapes are often needed notably for orthodontic and orthopedic devices. As an illustration of parts of orthodontic devices having a complex shape, orthodontic brackets, can be cited. As an illustration of parts of orthopedic devices having a complex shapes, hip rasps can be cited.

Parts of medical devices having a very low thickness are also often needed, notably for medical tubings, orthodontic devices, medical films and coatings.

Medical tubings, useful notably for catheters and guidewires, feature typically diameters that measure thousandths of an inch, with walls thinner than a human hair; to produce medical tubings with extremely thin walls, manufacturers force material to flow through the small orifices of processing equipment. As an illustration of parts of orthodontic devices having a very low thickness, orthodontic wires can be cited. As an illustration of medical coatings, biocidal coatings coated on the inner and/or outer walls of catheters can be cited.

Material selection is often crucial for medical devices. Engineering polymers, such as polyetheretherketones, polysulfones, polycarbonates, polyurethanes and polyamides, are generally preferred over metal because of their light weight and ability to be shaped into complex shapes and articles having a very low thickness, while exhibiting a reasonably good balance of properties.

An important problem when using the above engineered polymers for medical applications is that they do not generally achieve the desirable level of stiffness. It has already been attempted to solve this problem by providing medical devices, such as catheters, guidewires, orthodontic wires made of certain polyarylenes of the "first two generations".

WO 2005/102406 (to Boston Scientific Scimed) and WO 2006/037078 (to Cordis Corp.), the whole content of which is herein incorporated by reference, describe medical devices, such as catheters, made from certain rigid-rod polyparaphenylenes. Parmax® 1000, a rigid-rod poly-1,4-(benzoylphenylene) homopolymer of the first generation, was anciently developed and commercialized by Mississippi Polymer Technologies under the trademark Parmax® SRP (SRP for "Self-Reinforcing Polymers").

WO 2006/008739 (to the University of Connecticut) describes an orthodontic appliance including an orthodontic component, such as an orthodontic bracket or wire, comprising either Parmax® 1000 (namely, a rigid-rod polyparaphenylene), or Parmax® 1200, a random copolymer of benzoyl appended 4,4-phenylene (15 mol. % of the repeat units) and 1,3-phenylene (85 mol. % of the repeat units, now commercialized by Solvay Advanced Polymers as Primospire™ PR-120. This polyphenylene of the second generation, commonly referred to as kinked rigid-rod polyphenylene (because it comprises p-phenylene and m-phenylene repeat units), can be further characterized by the presence of a high amount of p-phenylene, rigid-rod forming units and a low amount of m-phenylene, kink-forming units.

Unfortunately, because of the intrinsic rigid nature of the so-proposed polyarylenes of the $1^{st}$ two generations, shaping them into articles having complex shapes or with a very low thickness by melt processing techniques such as injection molding or extrusion, was very difficult. For example, extruding them into medical tubings (with extremely thin walls) or orthodontic wires (with small diameters), is extremely difficult. In practice, such rigid-rod polyphenylene need to be solvent-casted into thin films from various solvent mixtures, such as NMP, with all the economic and environmental drawbacks linked to the use of solvents.

WO 02/072007 (to the University of Pennsylvania) describes various facially amphiphilic rigid-rod polyarylenes, which are generally reported to be suitable notably for being incorporated in, or attached to a catheter. In particular, WO 02/072007 describes polyparaphenylenes homopolymers substituted with polar groups (—P) and non polar groups (—NP), such as polymers having the general formula

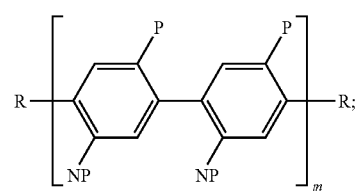

it describes also facially amphiphilic kinked polymetaphenylenes homopolymers substituted with polar groups (—P) and non polar groups (—NP), such as:

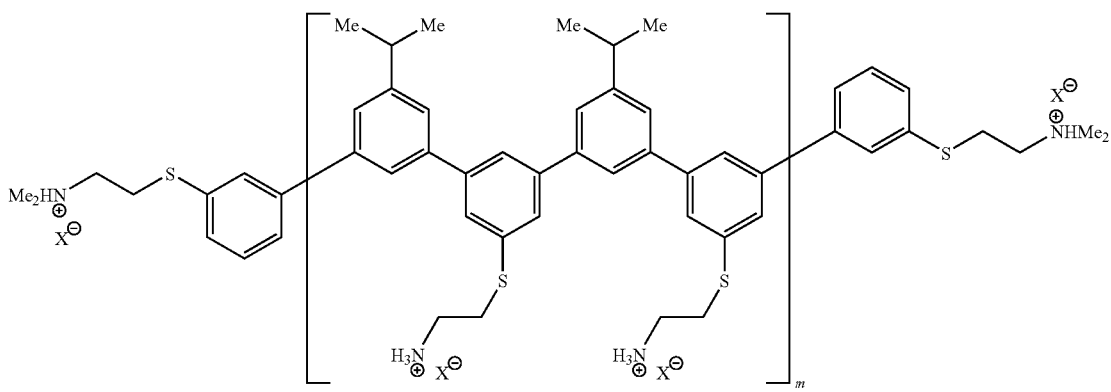

On the other hand, WO 02/072007 keeps totally silent on the mechanical properties, such as the stiffness, and melt-processability of the so-disclosed amphiphilic rigid-rod polyparaphenylenes and amphiphilic kink rigid-rod polymetaphenylenes. The Applicant, which has developed a big experience on polyphenylenes and their processing, is of the opinion that the amphiphilic rigid-rod polyparaphenylenes of WO'007 suffer from a poor processability, especially a poor injection-moldability and a poor extrudability, while the amphiphilic rigid-rod polyparaphenylenes of WO'007 exhibit a low stiffness, and, probably too, they further exhibit a poor processability, especially a poor injection-moldability and a poor extrudability.

Another important problem when using the above mentioned polymers for medical applications is that they do not generally achieve the desirable level of impact resistance (as typically characterized by standard notched and unnotched Izod tests).

In general some of, the above mentioned polyphenylenes, while offering an exceptionally high level of strength and stiffness (which often even exceeds the needs of the applications wherein they are used) suffer irremediably from a limited impact resistance. This property may be useful in certain demanding applications, such as articles used as medical devices.

There is thus an important need for medical devices including parts exhibiting a confluence of characteristics including high stiffness, high torqueability, high pushability, high flexibility and a very good impact resistance, and which can be easily formed by melt-processing techniques, such as extrusion or injection-molding, including when the parts of concern have a complex shape and/or a very low thickness (e.g. by using an extruder with extremely small orifices).

SUMMARY OF THE INVENTION

This need, and still other ones, are met by the present invention.

The medical devices of the present invention feature some unexpected advantages because of the materials of which they are made.

In a first aspect, the present invention concerns a medical device (Δ) comprising at least one part (π) consisting of a polymer material (M) comprising at least one kinked rigid-rod polyarylene (P) of which more than 50 wt. % of the recurring units are recurring units (R) of one or more formulae consisting of an optionally substituted arylene group, provided said optionally substituted arylene group is linked by each of its two ends to two other optionally substituted arylene groups via a direct C—C linkage, said recurring units (R) being a mix (μ) consisting of:
  between 0 and 75 mole %, based on the total number of moles of the recurring units (R), of rigid rod-forming arylene units (Ra), said rigid rod-forming arylene units (Ra) being optionally substituted by at least one monovalent substituting group,
with
  between 25 and 100 mole %, based on the total number of moles of the recurring units (R), of kink-forming arylene units (Rb), said kink-forming arylene units (Rb) being optionally substituted by at least one monovalent substituting group.

The kinked rigid-rod polyarylene (P) can be characterized by a high amount of kink-forming units and a low amount of rigid-rod forming units. It can from now on be reasonably viewed as a polyarylene of a new generation (the "third generation"), in that it is expected to provide an important breakthrough in the field of medical devices, and certain other high-tech applications. A kinked rigid-rod polyarylene (P) is now commercially available from Solvay Advanced Polymers, L.L.C. as PRIMOSPIRE™ PR-250 polyphenylene.

Another aspect of the present invention concerns a part (π) of a medical device (Δ), said part (π) consisting of a polymer material (M) comprising at least one kinked rigid-rod polyarylene (P) of which more than 50 wt. % of the recurring units are recurring units (R) of one or more formulae consisting of an optionally substituted arylene group, provided said optionally substituted arylene group is linked by each of its two ends to two other optionally substituted arylene groups via a direct C—C linkage, said recurring units (R) being a mix (μ) consisting of:
  between 0 and 75 mole %, based on the total number of moles of the recurring units (R), of rigid rod-forming arylene units (Ra), said rigid rod-forming arylene units (Ra) being optionally substituted by at least one monovalent substituting group,
with
  between 25 and 100 mole %, based on the total number of moles of the recurring units (R), of kink-forming arylene units (Rb), said kink-forming arylene units (Rb) being optionally substituted by at least one monovalent substituting group.

Still another aspect of the present invention concerns a method for the manufacture of the medical device (Δ) as above described, wherein the polymer material (M) is shaped into the part (π) by a melt-processing technique.

Still another aspect of the present invention concerns a method for the manufacture of the part (π) of a medical device (Δ) as above described, wherein the polymer material (M) is shaped into the part (π) by a melt-processing technique.

The melt-processing technique by which the polymer material (M) is shaped into the part (π), is preferably chosen from extrusion and injection-molding. A certain particular extrusion technique which may be useful for the purpose of the present invention is commonly known as "total intermittent extrusion", wherein medical articles, such as medical tubings, are produced as integral parts rather than separate pieces bonded together.

Still another aspect of the present invention is a method for therapeutically treating a human or animal patient, wherein the method comprises using the medical device (Δ) as above described.

Still another aspect of the present invention is a method for surgically treating a human or animal patient, wherein the method comprises using the medical device (Δ) as above described.

Still another aspect of the present invention is a method for diagnosing a human or animal patient, wherein the method comprises using the medical device (Δ) as above described.

DETAILED DESCRIPTION

The Medical Device (Δ)

The medical device (Δ) may consist of one part (the "single part"). Then, the single part is a part (π) consisting of the polymer material (M).

Alternatively, the medical device (Δ) may consist of several parts. The case being, either one part or several parts of the medical device (Δ) may be parts (π) consisting of the polymer material (M). When several parts of the medical device (Δ) consist of the polymer material (M) [parts (π)], each of them may consist of the same polymer material (M); alternatively, at least two parts (π) may differ from each other by the chemical nature of the polymer material (M).

The medical device (Δ) can be selected from the group of medical tubings (which include catheters and guidewires), orthodontic devices, orthopedic devices and diagnosis devices, and surgical devices.

In particular, the medical device (Δ) can be a medical device exactly as described in WO 2006/037078, the whole content of which is herein incorporated by reference, except that the rigid-rod polyphenylene included in the medical device of WO 2006/037078 is completely replaced, weight pro weight, by the kinked rigid-rod polyphenylene (P) as above described. In particular, the medical device (Δ) may be:
  a medical device (Δ1) for therapeutically treating a patient by advancing along a body passage to a desired site for treatment, comprising a flexible polymer component (π1) made of the kinked rigid-rod polyphenylene (P), wherein the component has sufficient strength and flexibility that the component has no reinforcement;
  the medical device (Δ1) as above described, which is a catheter, and the flexible polymer component (π1) is a catheter shaft defining a lumen;
  the medical device (Δ1) as above described, which is a catheter, and the flexible polymer component (π1,1) is a catheter shaft defining a lumen, and the catheter further comprises a balloon (π1,2) affixed to a distal end of the catheter shaft, wherein the balloon is made of the kinked rigid-rod polyphenylene (P);
  the medical device (Δ1) as above described, which is a guidewire;
  the medical device (Δ1) as above described, which is selected among the group of: balloon catheters, diagnostic catheters, guiding catheters, stent delivery system catheters, injection catheters, gene therapy catheters, electrophysiology catheters, therapeutic drug delivery catheters, ultrasound catheters, and laser angioplasty catheters;
  a balloon catheter (Δ2) comprising: a catheter shaft having a proximal and distal end, defining an inflation lumen; a polymer balloon affixed to the catheter shaft near the distal end, the inflation lumen communicating with an interior of the balloon; at least a portion (π2) of the balloon catheter being made of the kinked rigid-rod polyphenylene (P);
  a catheter (Δ3), comprising a tubular shaft member, at least a portion (π3) of the shaft member being made of the kinked rigid-rod polyphenylene (P).

The medical device (Δ) can be also be a medical device, such as a guidewire or a catheter, exactly as described in WO 2005/102406, the whole content of which is herein incorporated by reference, except that the thermoplastic rigid-rod polymer included in the medical device of WO 2005/102406 is completely replaced, weight pro weight, by the kinked rigid-rod polyphenylene (P) as above described. In particular, in accordance with embodiment (E2), the medical device (Δ) may be:
  a guidewire (Δ4) comprising: an atraumatic distal tip; a proximal end; an elongate core (π4) made from the kinked rigid-rod polyphenylene (P), the core extending from the atraumatic distal tip to the proximal end; and a polymeric sheath disposed over the core;
  a medical device (Δ5) comprising an elongate flexible element (π5) made from a first polymer which is the kinked rigid-rod polyphenylene (P);
  the medical device (Δ5) as above described, wherein it is an intravascular guidewire;
  the medical device (Δ5) as above described, wherein it is a catheter;
  the medical device (T5) as above described, wherein it is a catheter, the flexible elongate member being a first sleeve (π5,1), and the catheter further comprises a second sleeve (π5,2) disposed on the first, the second sleeve being made from the kinked rigid-rod polyphenylene (P).

For convenience, the parts comprising the kinked rigid-rod polyphenylene (P) have been labelled (π . . . ).

The medical device (Δ) can be also be a catheter, in which an amphiphilic kinked rigid-rod polyphenylene (P) has been incorporated, or to which an amphiphilic kinked rigid-rod polyphenylene (P) has been attached, exactly as described from p. 30, begin of last paragraph, to p. 31, end of second paragraph (pre- and post manufacture modification techniques). The recurring units (R) of the amphiphilic kinked rigid-rod polymer (P) are preferably a mix (μ) consisting of rigid rod-forming arylene units (Ra) and kink-forming arylene units (Rb) in appropriate amounts, wherein:
  recurring units (Ra) are selected from

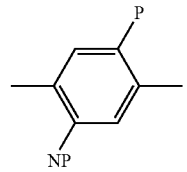

or a mix of

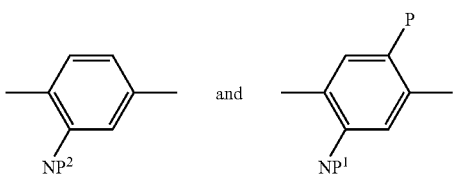

in a mole ratio of from 25:75 to 75:25, preferably from 60:40 to 40:60;

P being a polar group, such as:

P
O—CH$_2$—CH$_2$NMe$_2$
O—CH$_2$—CH$_2$-(2-pyridyl)
O—CH$_2$—CH$_2$N(CH$_2$—CH$_2$—NMe$_2$)$_2$
O—CH$_2$—CH$_2$-(2-imidazolyl)
O—CH$_2$—CH$_2$NH—C(=NH)NH$_2$
O—CH$_2$—CH$_2$N(CH$_2$CH$_2$)$_2$NH NP, NP1 and NP2 being non polar groups, such as
. . .
—CH$_2$CH$_3$
O—CH$_2$CHMe$_2$
O—CHMe$_2$
OCMe$_3$
O—CH$_3$—CHMe$_2$
O(CH$_2$)$_2$Me In a preferred embodiment, the medical device (Δ) is an orthodontic appliance (Δ6) including at least one orthodontic component (π6) comprising a rigid backbone polymer, exactly as described in WO 2004/004592, the whole content of which is herein incorporated by reference, except that the rigid backbone polymer included in the medical device of WO 2004/004592 is completely replaced, weight pro weight, by the kinked rigid-rod polyphenylene (P) as above described. Correspondingly, a preferred part (π) of a medical device (Δ) is the orthodontic component (π6), as above described. The orthodontic component (Δ6) is very preferably selected from the group consisting of orthodontic brackets, orthodontic wires and orthodontic aligners.

Orthodontic appliances are used to move or manipulate certain teeth to correct irregularities and/or abnormalities in their relationships with surrounding members. There are three main types of orthodontic appliances: active, passive and functional. All these types can be fixed or removable. Active orthodontic appliances are devices used to apply forces to the teeth to change the relationship of the teeth. Passive orthodontic appliances include space maintainers and retainers while functional orthodontic appliances, also known as dentofacial orthopedic appliances, utilize the muscle action of the patient to produce orthodontic or orthopedic forces.

Orthodontic appliances include systems comprising wires and brackets as well as systems comprising removable aligners. This manipulation is achieved by the application of designed force systems to selected teeth. The forces for these systems are provided by a force delivery component such as an arch wire or spring. The wire is elastically deformed, or activated, to absorb energy. The wire slowly releases this energy as it deactivates and returns to the relaxed condition. The released energy is applied to selected teeth, for instance by interaction of the loaded wire with brackets attached to the teeth, to provide the desired tooth movement.

An orthodontic bracket is intended to denote an orthodontic attachment that is secured to a tooth (either by bonding or banding) for the purpose of engaging an arch wire. Orthodontic wires, also called arch wires, are wires engaged in orthodontic attachments, affixed to the crowns of two or more teeth, and capable of causing or guiding tooth movement.

There are several criteria that are important for orthodontic appliances in general. For example, the orthodontic material must be non-toxic, resistant to the corrosive environment within a patient's mouth and available in desired shapes and dimensions. Some other important parameters, especially for orthodontic force delivery components, include strength, elastic deformation, yield, strength, stiffness, formability and joinability. More recently, the aesthetic appearance of orthodontic components has become very important, with many patients expressing a strong preference for orthodontic components and appliances that are less visually apparent against the patients teeth.

Some specific orthodontic components, such as a wire, require sufficient ductility to be formed to a desired customized shape for a particular patient. Additionally, the wire has to be joinable to other wires or components, while retaining its strength and elasticity characteristics. Naturally, the wire must be available in a variety of desired cross-sectional shapes and dimensions as variability in cross-sectional shape can allow greater potential control of orthodontic force systems.

Some orthodontic components, such as attachments, that translate the force from the wire directly to the tooth have additional criteria that have to be considered. For example, the design, geometry and overall dimensions of an attachment such as a bracket are important for both its ease of manipulation as well as its ability to help contribute to effective application of the orthodontic force system. Attachments may be bonded directly to the tooth surface or mechanically fastened using a band that typically circumscribes the entire tooth. Attachments must have sufficient strength to transfer force to the joined tooth without attachment deformation or fracture. Additionally, it is desirable for the bracket to be comprised of a material that provides a low level of friction to wires within the slot.

Another approach to orthodontic tooth movement is the use of a removable appliance, such as an aligner, in place of wires and brackets. Such aligners can be very aesthetic since they are removable by the patient and require no bonding of attachments.

The Part (π)

Non limitative examples of parts (π) in accordance with the present invention have already been above described, when describing the medical device (Δ).

The choice of the kinked rigid-rod polyphenylene (P) as ingredient of the polymer material (M) for the manufacture of the part (π) is especially beneficial when the part (π) is an essentially at most two-dimensional part.

The part (π) is preferably an essentially at most two dimensional part.

From a practical point of view, any part is three-dimensional, and can thus be characterized notably by three characteristic dimensions ("length", "width" and "height"). However, some parts are such that one or two of their characteristic dimensions is (are) considerably lower than respectively the other two ones or the third one. Here and wherever else used in the present description, the terms "considerably lower" should advantageously be understood as "more than 10 times lower" and preferably as "more than 100 times lower". These parts are herein named "essentially at most two-dimensional parts".

Essentially at most two-dimensional parts include films (meaning "uncoated films"), coatings, filaments and hollow bodies such as tubes and tubings. The coatings may be coated on a filament, on a hollow body, on film, plaque or slab, and so on.

The thickness of a part of a regular or irregular volume can be defined as:

$$t = \int V \tau(x,y,z) dx dy dz / V,$$

wherein x, y and z are the coordinates of an elementary volume dV (dV being equal to dx times dy times dz) of the part of overall plain volume V, and τ is the local thickness.

The local thickness τ, associated to a material point of coordinates (x, y, z), is defined as the length of the shortest straight line D including the material point of concern, which goes right through the part (i.e. which goes from the material point where D enters the part to the material point where D exits the part).

The thickness of the part may be of less than 500 µm, less than 200 µm, less than 100 µm, less than 50 µm, less than 30 µm, less than 20 µm, less than 10 µm, less than 8 µm, less than 6 µm, less than 4 µm, less than 2 µm or less than 1 µm. It may be of above 0.1 µm, above 1 µm, above 2 µm, above 5 µm, above 10 µm, above 20 µm or above 50 µm.

The Kinked Rigid-Rod Polyarylene (P)

For the purpose of the present invention, an arylene group is a hydrocarbon divalent group consisting of one core composed of one benzenic ring or of a plurality of benzenic rings fused together by sharing two or more neighboring ring carbon atoms, and of two ends.

Non limitative examples of arylene groups are phenylenes, naphthylenes, anthrylenes, phenanthrylenes, tetracenylenes, triphenylylenes, pyrenylenes, and perylenylenes. The arylene groups (especially the numbering of the ring carbon atoms) were named in accordance with the recommendations of the CRC Handbook of Chemistry and Physics, 64$^{th}$ edition, pages C1-C44, especially p. C11-C12.

Arylene groups present usually a certain level of aromaticity; for this reason, they are often reported as "aromatic" groups. The level of aromaticity of the arylene groups depends on the nature of the arylene group; as thoroughly explained in Chem. Rev. 2003, 103, 3449-3605, "Aromaticity of Polycyclic Conjugated Hydrocarbons", the level of aromaticity of a polycyclic aromatic hydrocarbon can be notably quantified by the "index of benzene character" B, as defined on p. 3531 of the same paper; values of B for a large set of polycyclic aromatic hydrocarbon are reported on table 40, same page.

An end of an arylene group is a free electron of a carbon atom contained in a (or the) benzenic ring of the arylene group, wherein an hydrogen atom linked to said carbon atom has been removed. Each end of an arylene group is capable of forming a linkage with another chemical group. An end of an arylene group, or more precisely the linkage capable of being formed by said end, can be characterized by a direction and by a sense; to the purpose of the present invention, the sense of the end of an arylene group is defined as going from the inside of the core of the arylene group to the outside of said core. As concerns more precisely arylene groups the ends of which have the same direction, such ends can be either of the same or opposite sense; also, their ends can be in the straight foregoing of each other, or not (otherwise said, they can be disjoint).

A polyarylene is intended to denote a polymer of which more than 50 wt. % of the recurring units are recurring units (R) of one or more formulae consisting of an optionally substituted arylene group, provided said optionally substituted arylene group is linked by each of its two ends to two other optionally substituted arylene groups via a direct C—C linkage. That the optionally substituted arylene group is linked by each of its two ends to two other optionally substituted arylene groups via a direct C—C linkage, is an essential feature of the recurring units (R); thus, an arylene recurring unit which is linked by at least one of its two ends to a group other than an arylene group such as phenylene recurring units $\phi_1$, $\phi_2$ and $\phi_{2'}$ below:

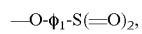

—O-$\phi_1$-S(=O)$_2$,

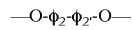

—O-$\phi_2$-$\phi_{2'}$-O— are not recurring units (R) in the sense of the present invention.

The arylene groups of which the recurring units (R) consist can be unsubstituted. Alternatively, they can be substituted by at least one monovalent substituting group.

The monovalent substituting group is usually not polymeric in nature; its molecular weight is preferably below 500, more preferably below 300, still more preferably below 200 and most preferably below 150.

The monovalent substituting group is advantageously a solubilizing group. A solubilizing group is one increasing the solubility of the polyarylene in at least one organic solvent, in particular in at least one of dimethylformamide, N-methylpyrrolidinone, hexamethylphosphoric triamide, benzene, tetrahydrofuran and dimethoxyethane, which can be used as solvents during the synthesis of the polyarylene by a solution polymerization process.

The monovalent substituting group is also advantageously a group which increases the fusibility of the polyarylene, i.e. it lowers its glass transition temperature and its melt viscosity, so as to desirably make the polyarylene suitable for thermo-processing.

Preferably, the monovalent substituting group is chosen from:

hydrocarbyls such as alkyls, aryls, alkylaryls and aralkyls;
halogenos such as —Cl, —Br, —F and —I;
hydrocarbyl groups partially or completely substituted by at least one halogen atom such as halogenoalkyls, halogenoaryls, halogenoalkylaryls and halogenoaralkyls;
hydroxyl;
hydrocarbyl groups substituted by at least one hydroxyl group, such as hydroxyalkyls, hydroxyaryls, hydroxyalkylaryls and hydroxyaralkyls;
hydrocarbyloxys [—O—R, where R is a hydrocarbyl group], such as alkoxys, aryloxys, alkylaryloxys and aralkyloxys;
amino (—NH$_2$)
hydrocarbyl groups substituted by at least one amino group, such as aminoalkyls and aminoaryls;
hydrocarbylamines [—NHR or NR$_2$, where R is a hydrocarbyl group] such as alkylamines and arylamines;
carboxylic acids and their metal or ammonium salts, carboxylic acid halides, carboxylic anhydrides;
hydrocarbyl groups substituted by at least one of carboxylic acids, metals or ammonium salts thereof, carboxylic acid halides and carboxylic anhydrides, such as —R—C(=O)OH where R is an alkyl or an aryl group;
hydrocarbylesters [—C(=O)OR or —O—C(=O)R, where R is a hydrocarbyl group] such as alkylesters, arylesters, alkylarylesters and aralkylesters; amido [—C(=O)NH$_2$];
hydrocarbyl groups substituted by at least one amido group;
hydrocarbylamide monoesters [—C(=O)NHR or —NH—C(=O)—R, where R is a hydrocarbyl group], such as alkylamides, arylamides, alkylarylamides and aralkylamides, and hydrocarbylamide diesters [—C(=O)NR$_2$ or —N—C(=O)R$_2$, where R are a hydrocarbyl groups], such as dialkylamides and diarylamides;

sulfinic acid (—SO$_2$H), sulfonic acid (—SO$_3$H), their metal or ammonium salts, hydrocarbylsulfones [—S(O)$_2$—R, where R is the hydrocarbyl group], such as alkylsulfones, arylsulfones, alkylarylsulfones, aralkylsulfones;

aldehyde [—C(=O)H] and haloformyls [—C(=O)X, wherein X is a halogen atom];

hydrocarbylketones [—C(=O)—R, where R is a hydrocarbyl group], such as alkylketones, arylketones, alkylarylketones and aralkylketones;

hydrocarbyloxyhydrocarbylketones [—C(=O)—R$^1$—O—R$^2$, where R$^1$ is a divalent hydrocarbon group such as an alkylene, an arylene, an alkylarylene or an aralkylene, preferably a C$_1$-C$_{18}$ alkylene, a phenylene, a phenylene group substituted by at least one alkyl group, or an alkylene group substituted by at least one phenyl group; and R$^2$ is a hydrocarbyl group, such as an alkyl, aryl, alkylaryl or aralkyl group], such as alkyloxyalkylketones, alkyloxyarylketones, alkyloxyalkylarylketones, alkyloxyaralkylketones, aryloxyalkylketones, aryloxyarylketones, aryloxyalkylarylketones and aryloxyaralkylketones;

any of the above groups comprising at least one hydrocarbyl group or a divalent hydrocarbon group R$^1$, wherein said hydrocarbyl group or said R$^1$ is itself substituted by at least one of the above listed monovalent substituting groups, e.g. an arylketone —C(=O)—R, where R is an aryl group substituted by one hydroxyl group;

where:

the hydrocarbyl groups contain preferably from 1 and 30 carbon atoms, more preferably from 1 to 12 carbon atoms and still more preferably from 1 to 6 carbon atoms;

the alkyl groups contain preferably from 1 to 18 carbon atoms, and more preferably from 1 to 6 carbon atoms; very preferably, they are chosen from methyl, ethyl, n-propyl, isopropyl, n-butyl, isobutyl and tert-butyl;

the aryl groups are defined as monovalent groups consisting of one end and one core composed of one benzenic ring (such the phenyl group) or of a plurality of benzenic rings directly linked to each other via a carbon-carbon linkage (such as the biphenyl group) or fused together by sharing two or more neighboring ring carbon atoms (such as the naphthyl groups), and wherein the ring carbon atoms are possibly substituted by at least one nitrogen, oxygen or sulfur atom preferably, in the aryl groups, no ring carbon atom is substituted;

the aryl groups contain preferably from 6 to 30 carbon atoms; more preferably, they are phenyl groups;

the alkyl group which is contained in the alkylaryl groups meets the preferences of the alkyl groups as above expressed;

the aryl group which is contained in the aralkyl groups meets the preferences of the aryl groups as above expressed.

More preferably, the monovalent substituting group is chosen from hydrocarbylketones [—C(=O)—R, where R is a hydrocarbyl group] and hydrocarbyloxyhydrocarbylketones [—C(=O)—R$^1$—O—R$^2$, where R$^1$ is a divalent hydrocarbon group and R$^2$ is a hydrocarbyl group], said hydrocarbylketones and hydrocarbyloxyhydrocarbylketones being unsubstituted or substituted by at least one of the above listed monovalent substituting groups.

Still more preferably, the monovalent substituting group is chosen from arylketones and aryloxyarylketones, said arylketones and aryloxyarylketones being unsubstituted or substituted by at least one of the above listed monovalent substituting groups.

Most preferably, the monovalent substituting group is an (unsubstituted) arylketone, in particular it is phenylketone [—C(=O)-phenyl].

The core of the optionally substituted arylene group of the recurring units (R) is composed of preferably at most 3, more preferably at most 2, and still more preferably at most one benzenic ring. Then, when the core of the optionally substituted arylene group of the recurring units (R) is composed of one benzenic ring, the recurring units (R) are of one or more formulae consisting of an optionally substituted phenylene group, provided said optionally substituted phenylene group is linked by each of its two ends to two other optionally substituted arylene groups via a direct C—C linkage.

As above explained, the optionally substituted arylene group of the recurring units (R) is linked by each of its two ends to two other optionally substituted arylene groups via a direct C—C linkage. Preferably, it is linked by each of its two ends to two other optionally substituted phenylene groups via a direct C—C linkage.

As also above explained, both ends of the optionally substituted arylene group of the recurring units (R) can be characterized notably by a direction and by a sense.

A first set of recurring units (R) is composed of optionally substituted arylene groups, the ends of which
have the same direction,
are of opposite sense, and
are in the straight foregoing of each other
[hereafter, rigid rod-forming arylene units (Ra)].

Non limitative examples of such optionally substituted arylene groups include:

1,4-phenylene
(also named p-phenylene)

1,4-naphtylene

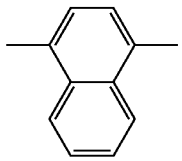

1,4-phenanthrylene and
2,7-phenanthrylene
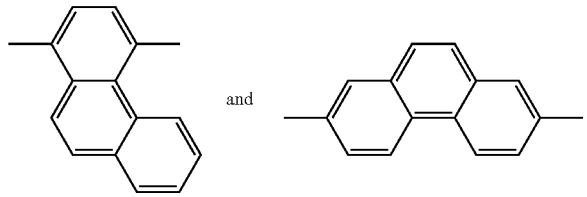
1,4-anthrylene and
9,10-anthrylene
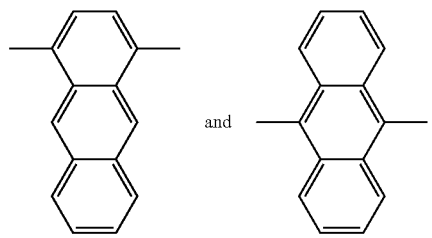
2,7-pyrenylene
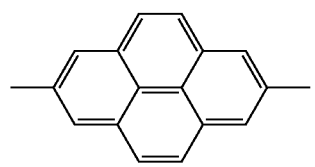
1,4-naphthacenylene and
5,12-naphthacenylene
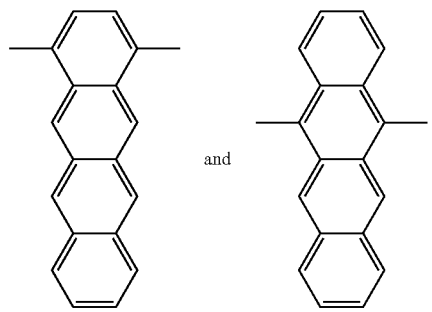
1,4-chrysenylene
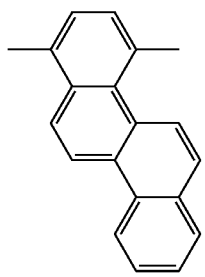
1,4-triphenylylene and
2,7-triphenylylene
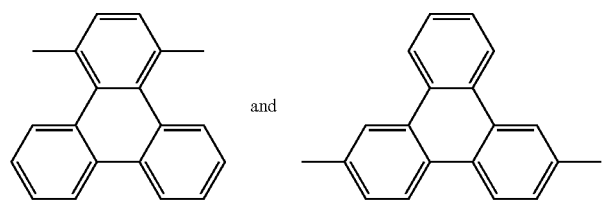

1,4-pentacenylene,
5,14-pentacenylene and
6,13-pentacenylene

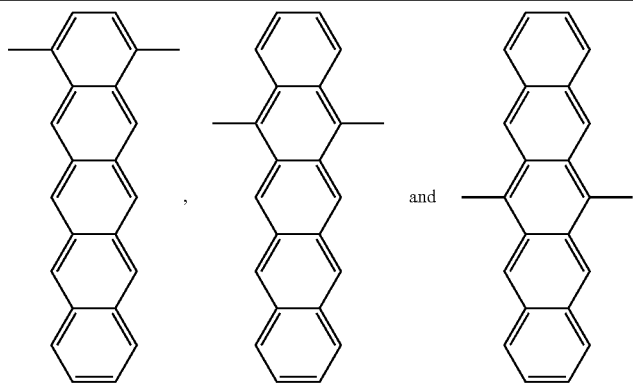

1,6-coronenylene

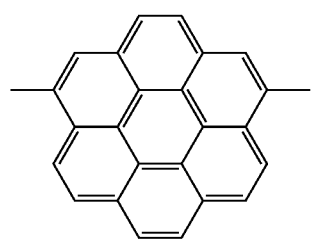

1,4-trinaphthylenylene,
2,9-trinaphthylenylene and
5,18-trinaphthylenylene

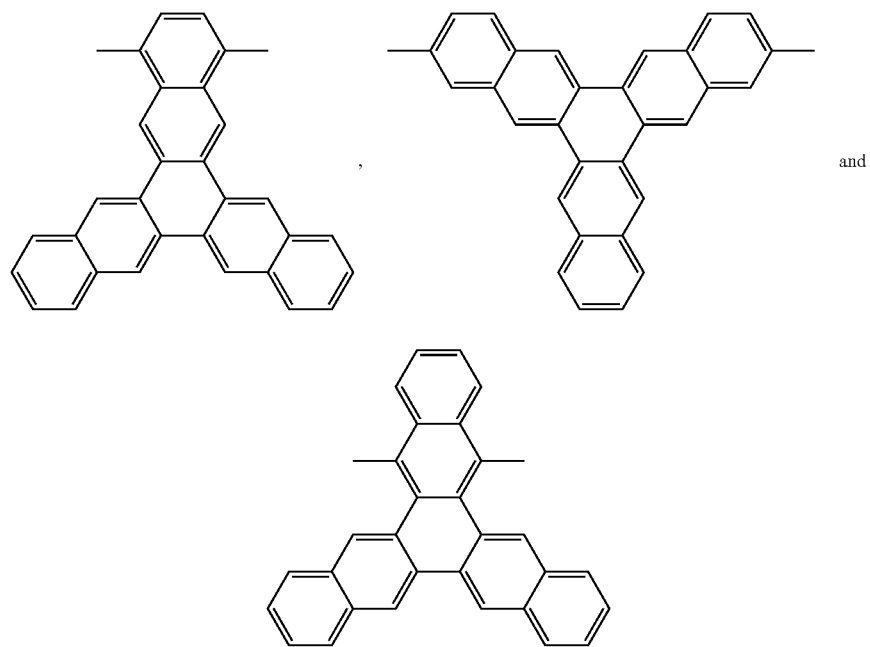

and any of these groups substituted by at least one monovalent substituting groups as above defined, in particular by a phenylketone group.

Optionally substituted p-phenylenes are preferred as rigid rod-forming arylene units (Ra).

Rigid rod-forming arylene units (Ra), when contained in the polyarylenes, result in straight polymer chains exhibiting an outstanding rigidity. For this reason, such polyarylenes are commonly referred to as "rigid-rod polymers".

A second set of recurring units (R) is composed of optionally substituted arylene groups, the ends of which either have a different direction, forming thus together an angle between 0 and 180°, said angle being possibly acute or obtuse, or have the same direction and the same sense, or have the same direction, are of opposite sense and are disjoint (i.e. not in the straight foregoing of each other) [globally hereafter referred to as kink-forming arylene units (Rb)].

Then, a first subset of kink-forming arylene units (Rb) is composed of optionally substituted arylene groups, the ends of which have a different direction, forming together an acute angle [kink-forming arylene units (Rb-1)]. Non limitative examples of optionally substituted arylene groups the ends of which have a direction different from each other include:

| | |
|---|---|
| 1,2-phenylene (or o-phenylene) | 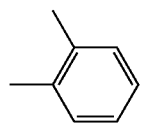 |
| 1,2-, 2,3- and 1,7-naphtylenes | 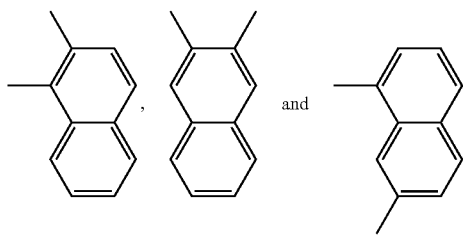 |
| 1,2-, 1,8-, 1,9-, 2,3-, 2,5- and 2,10-phenanthrylenes | 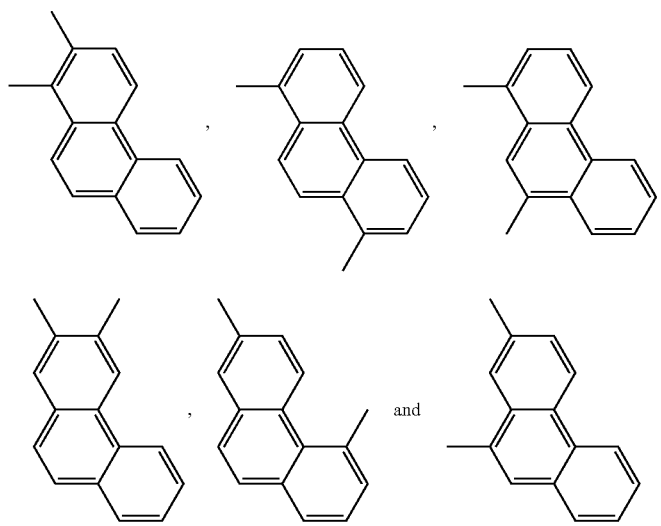 |
| 1,2- and 1,7-anthrylenes | 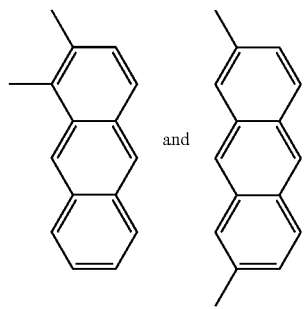 | and any of these groups substituted by at least one monovalent substituting group, as above defined, in particular by a phenylketone group.

A second subset of kink-forming arylene units (Rb) is composed of optionally substituted arylene groups, the ends of which have a different direction, forming together an obtuse angle [kink-forming units (Rb–2)]. Non limitative examples of optionally substituted arylene groups the ends of which have a direction different from each other include:

| | |
|---|---|
| 1,3-phenylene (or m-phenylene) | 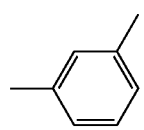 |

| | |
|---|---|
| 1,3- and 1,6-naphtylenes | 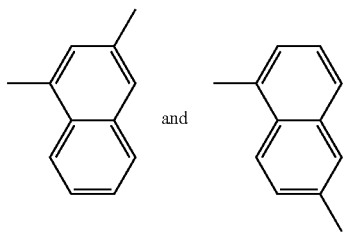 |
| 1,3-, 1,5-, 1,7-, 2,4-, 2,9- and 3,10-phenanthrylenes | 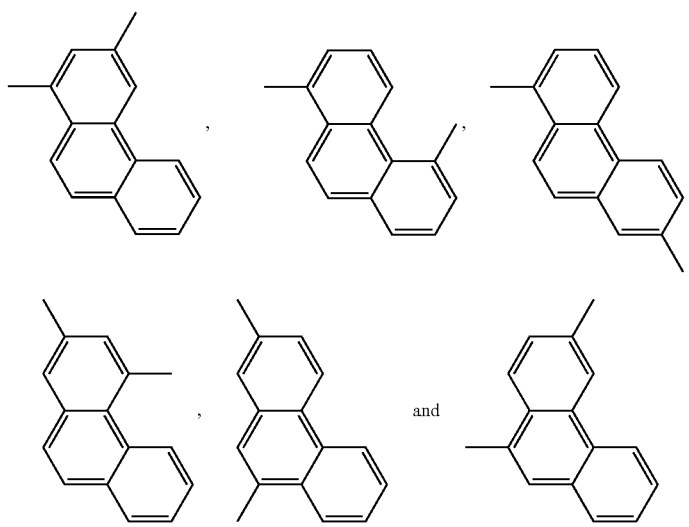 |
| 1,3- and 1,6-anthrylenes | 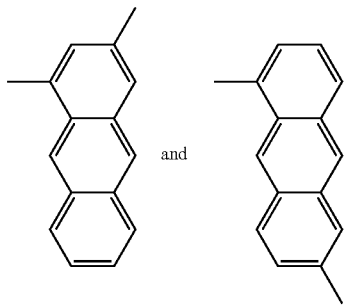 | and any of these groups substituted by at least one monovalent substituting group, as above defined, in particular by a phenylketone group.

A third subset of kink-forming arylene units (Rb) is composed of optionally substituted arylene groups, the ends of which have the same direction and the same sense [kink-forming arylene units (Rb–3)]. Non limitative examples of optionally substituted arylene groups the ends of which the same direction and the same sense include:

| | |
|---|---|
| 1,8-naphthylene | 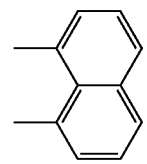 |

1,10- and 3,5-phenanthrylenes

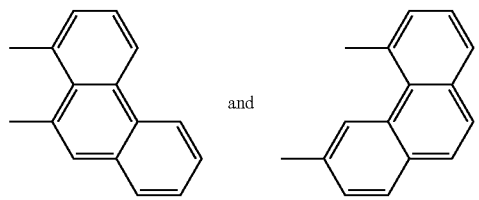

and 1,8- and 1,9-anthrylenes

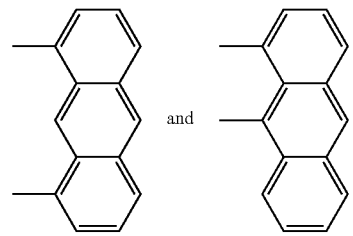

and and any of these groups substituted by at least one monovalent substituting group, as above defined, in particular by a phenylketone group.

A fourth subset of kink-forming arylene units (Rb) is composed of optionally substituted arylene groups, the ends of which have the same direction, are of opposite sense and are disjoint [kink-forming arylene units (Rb–4)]. Non limitative examples of such optionally substituted arylene groups include:

arylene units (Rb–1). Even still more preferably, kink-forming arylene units (Rb) are optionally substituted m-phenylenes.

Kink-forming arylene units (Rb), when contained in the polyarylene, result in more or less kinked polymer chains, exhibiting a higher solubility and fusibility than straight polymer chains. For this reason, such polyarylenes are commonly referred to as "kinked polymers".

1,5- and 2,6-naphtylenes

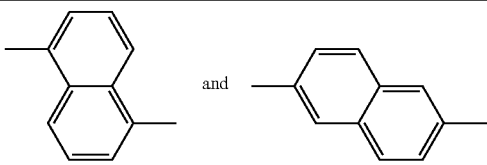

and 1,6-, 3,9- and 4,10-phenanthrylenes

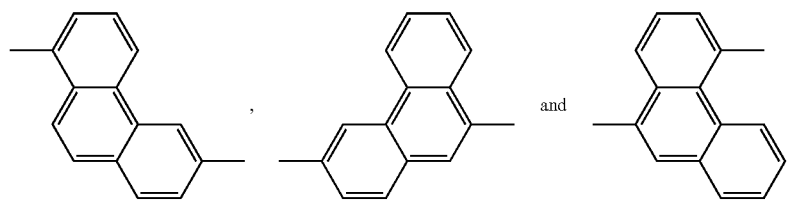

, and 1,5-, 1,10- and 2,6-anthrylenes

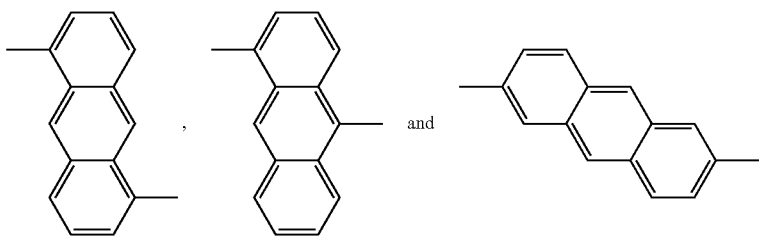

, and and any of these groups substituted by at least one monovalent substituting group, as above defined, in particular by a phenylketone group. Preferably, kink-forming arylene units (Rb) are chosen from kink-forming arylene units (Rb–1), kink-forming arylene units (Rb–2) and kink-forming arylene units (Rb–4). More preferably, kink-forming arylene units (Rb) are chosen from kink-forming arylene units (Rb–1) and kink-forming arylene units (Rb–2). Still more preferably, kink-forming arylene units (Rb) are chosen from kink-forming The recurring units (R) of the kinked rigid-rod polyarylene (P) must be of a specific type, namely they must be a mix (μ) consisting of:

between 0 and 75 mole %, based on the total number of moles of recurring units (R), of rigid rod-forming arylene units (Ra), said rigid rod-forming arylene units (Ra) being optionally substituted by at least one monovalent substituting group with between 25 and 100 mole %, based on the total number of moles of recurring units (R), of kink-forming arylene units (Rb), said kink-forming arylene units being optionally substituted or not by at least one monovalent substituting group, The recurring units (R) are preferably a mix (μ) consisting of:
between 0 and 75 mole %, based on the total number of moles of recurring units (R), of rigid rod-forming arylene units (Ra) chosen from optionally substituted p-phenylenes,
with
between 25 and 100 mole %, based on the total number of moles of recurring units (R), of kink-forming arylene units (Rb) chosen from (i) optionally substituted m-phenylenes and (ii) mixes of optionally substituted m-phenylenes with optionally substituted o-phenylenes.

Preferably, essentially all, if not all, the rigid rod-forming arylene units (Ra) of the mix (μ) are p-phenylene units substituted by at least one substituting group. More preferably, essentially all, if not all, the rigid rod-forming arylene units (Ra) of the mix (μ) are p-phenylenes substituted by at least one monovalent substituting group chosen from hydrocarbylketones [—C(=O)—R, where R is a hydrocarbyl group] and hydrocarbyloxyhydrocarbylketones [—C(=O)—R$^1$—O—R$^2$, where R$^1$ is a divalent hydrocarbon group and R$^2$ is a hydrocarbyl group], said hydrocarbylketones and hydrocarbyloxyhydrocarbylketones being themselves unsubstituted or substituted by at least one monovalent substituting group as those above listed. Still more preferably, essentially all, if not all, the rigid rod-forming arylene units (Ra) of the mix (μ) are p-phenylenes substituted by at least one monovalent substituting group chosen from arylketones and aryloxyarylketones, said arylketones and aryloxyarylketones being unsubstituted or substituted by at least one monovalent substituting group as those above listed. Most preferably, essentially all, if not all, the rigid rod-forming arylene units (Ra) of the mix (μ) are p-phenylenes substituted by an arylketone group, in particular by the phenylketone group.

Essentially all, if not all, the kink-forming arylene units (Rb) of the mix (μ) are m-phenylene units optionally substituted by at least one substituting group. More preferably, essentially all, if not all, the kink-forming arylene units (Rb) of the mix (μ) are m-phenylene units which are optionally substituted by at least one monovalent substituting group chosen from hydrocarbylketones [—C(=O)—R, where R is a hydrocarbyl group] and hydrocarbyloxyhydrocarbylketones [—C(=O)—R$^1$—O—R$^2$, where R$^1$ is a divalent hydrocarbon group and R$^2$ is a hydrocarbyl group], said hydrocarbylketones and hydrocarbyloxyhydrocarbylketones being themselves unsubstituted or substituted by at least one monovalent substituting group as those above listed. Still more preferably, essentially all, if not all, the kink-forming arylene units (Rb) of the mix (μ) are unsubstituted m-phenylene units.

In the mix (μ), the number of moles of the kink-forming arylene units (Rb), based on the total number of moles of the recurring units (R), is preferably of at least 30%, more preferably at least 35%, still more preferably at least 40% and most preferably at least 45%. On the other hand, in the mix (μ), the number of moles of the kink-forming arylene units (Rb), based on the total number of moles of the recurring units (R), is preferably of at most 90%, more preferably at most 75%, still more preferably at most 65% and most preferably at most 55%.

Good results were obtained when the recurring units (R) were a mix consisting of p-phenylene units substituted by a phenylketone group with unsubstituted m-phenylene units, in a mole ratio of about 50:50.

The kinked rigid-rod polyarylene (P) may further comprise recurring units (R*), different from recurring units (R).

Recurring units (R*) may contain or not at least one strong divalent electron withdrawing group linked on each of its ends to an arylene group. Non limitative examples of recurring units (R*) free of such strong divalent electron withdrawing group are:

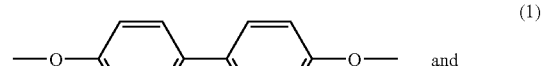 (1)

and

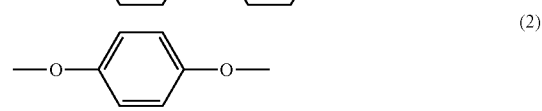 (2)

Recurring units (R*) contain preferably at least one strong divalent electron withdrawing group linked on each of its ends to an arylene group, in particular a p-phenylene group. The divalent electron withdrawing group is preferably chosen from the sulfone group [—S(=O)$_2$—], the carbonyl group [—C(=O)—], the vinylene group [—CH=CH—], the sulfoxide group [—S(=O)—], the azo group [—N=N—], saturated fluorocarbon groups like —C(CF$_3$)$_2$—, organic phosphine oxide groups [—P(=O)(=R$_h$)—, where R$_h$ is a hydrocarbyl group] and the ethylidene group [—C(=CA$_2$)—, where A can be hydrogen or halogen]. More preferably, the divalent electron withdrawing group is chosen from the sulfone group and the carbonyl group. Still more preferably, recurring units (R*) are chosen from:

(i) recurring units of formula

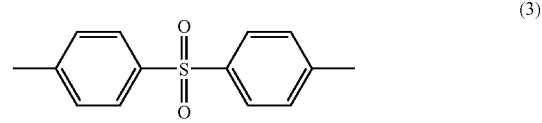 (3)

(ii) recurring units of formula

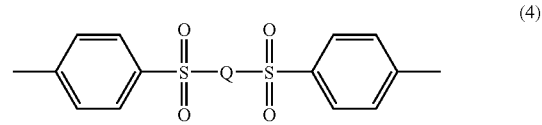 (4)

wherein Q is a group chosen from:

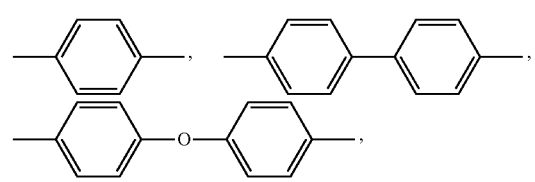

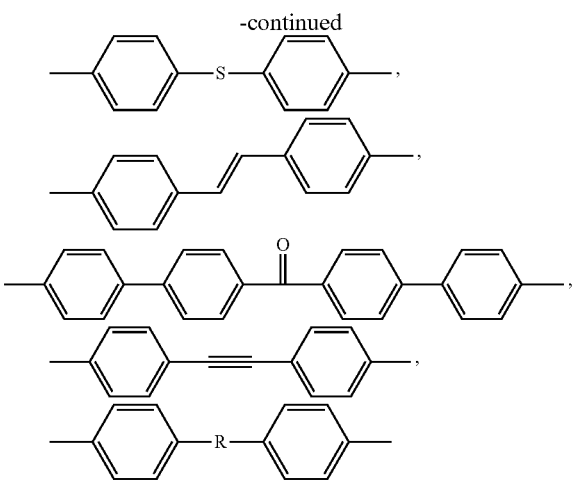

with R being:

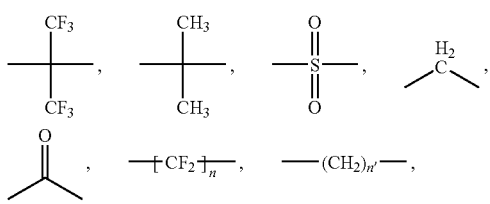

with n being an integer from 1 to 6 and n' being an integer from 2 to 6, Q being preferably chosen from

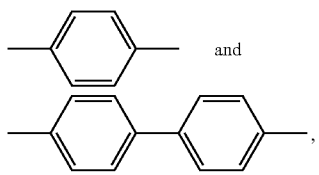

(iii) recurring units of formula

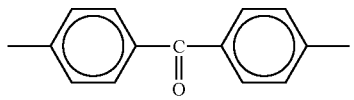
(5)

(iv) recurring units or formula

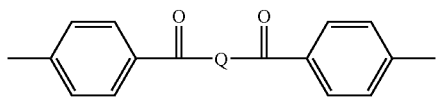
(6)

Preferably more than 75 wt. % and more preferably more than 90 wt. % of the recurring units of the polyarylene are recurring units (R). Still more preferably, essentially all, if not all, the recurring units of the polyarylene are recurring units (R).

Excellent results were obtained when the polyarylene was a kinked rigid-rod polyphenylene, essentially all, if not all, the recurring units of which consisted of a mix of p-phenylene substituted by a phenylketone group with unsubstituted m-phenylene in a mole ratio p-phenylene:m-phenylene of from 10:90 to 70.30, preferably of from 25:75 to 65:35, more preferably of from 35:65 to 60:40, still more preferably of from 45:55 to 55:45, and most preferably of about 50:50. Such a kinked rigid-rod polyphenylene is commercially available from Solvay Advanced Polymers, L.L.C. as PRIMOSPIRE™ PR-250 polyphenylene.

The kinked rigid-rod polyarylene (P) has usually a number average molecular weight greater than 1000, preferably greater than 5000, more preferably greater than about 10000 and still more preferably greater than 15000. On the other hand, the number average molecular weight of the kinked rigid-rod polyarylene is usually below 100000, and preferably below 70000. In a certain embodiment, the number average molecular weight of the kinked rigid-rod polyarylene is above 35000. In another embodiment, it is of at most 35000; in this embodiment, it is often of at most 25000 and sometimes of at most 20000. The number average molecular weight of a polyarylene in general, and in particular that of the kinked rigid-rod polyarylene (P), is advantageously determined by: (1) measuring a "relative" number average molecular weight of the polyarylene by Gel Permeation Chromatography (GPC) using polystyrene calibration standards, then (2) dividing the so-measured "relative" number average molecular weight by a factor 2. It is proceeded accordingly because the skilled in the art who is a specialist of polyarylenes knows that their "relative" number average molecular weight, as measured by GPC, are generally off by a factor of about 2 times; it has already been accounted for this correction factor in all the above cited lower and upper limits of molecular weight.

It can be amorphous (i.e. it has no melting point) or semi-crystalline (i.e. it has a melting point). It is preferably amorphous.

It has a glass transition temperature of advantageously above 50° C., preferably above 120° C. and more preferably above 150° C.

The kinked rigid-rod polyarylene (P) is generally unbranched. In particular, it is generally essentially free, or even free, of recurring branching units

wherein Ary is a polyvalent arylene and x represents the number of bonds beyond two, $x \geq 1$.

The kinked rigid-rod polyarylene (P) can be prepared by any method. A method well known in the art to prepare such kinked rigid-rod polyarylene comprises polymerizing, preferably by reductive coupling, (i) at least one dihaloarylene molecular compound consisting of an optionally substituted rigid rod-forming arylene group, which is linked on each of its two ends to one halogen atom, such as chlorine, bromine and iodine, with (ii) at least one dihaloarylene molecular compounds consisting of an optionally substituted kink-forming arylene group, which is linked on each of its two ends to one halogen atom, such as chlorine, bromine, iodine, and fluorine. The elimination of the halogen atoms from the dihaloarylene molecular compounds results in the formation of respectively optionally substituted rigid rod-forming and optionally substituted kink-forming arylene groups.

Thus, for example:
the elimination of both chlorine atoms from a molecule of p-dichlorobenzene, p-dichlorobiphenyl or their homologous of general formula Cl-($\phi$)$_N$—Cl, N being an integer from 3 to 10, results in the formation of respectively 1, 2 or N adjacent p-phenylene units (rigid rod-forming arylene units); thus, p-dichlorobenzene, p-dichlorobiphenyl and their homologous of general formula Cl-($\phi$)$_N$—Cl, N as above defined, can be polymerized, so as to form p-phenylene units;
2,5-dichlorobenzophenone (p-dichlorobenzophenone) can be polymerized, so as to form 1,4-(benzoylphenylene) units (also rigid rod-forming arylene units),
m-dichlorobenzene can be polymerized, so as to form m-phenylene units (kink-forming arylene units).

In the present invention, one, two, three, or even more than three different kinked rigid-rod polyarylenes (P) can be used.
Optional Ingredients The above described polymer material (M) may further contain one or more polymers other than the kinked rigid-rod polyarylene (P), and/or one or more non polymeric additives, collectively called optional ingredients.

The non polymeric additives of concern include notably fibrous reinforcing agents, particulate fillers and nucleating agents such as talc and silica, adhesion promoters, compatibilizers, curing agents, lubricants, metal particles, mold release agents, organic and/or inorganic pigments like TiO$_2$ and carbon black, dyes, flame retardants, smoke-suppressing agents, heat stabilizers, antioxidants, UV absorbers, tougheners such as rubbers, plasticizers, anti-static agents, melt viscosity depressants, and mixtures thereof.

In a first particular embodiment, the polymer material (M) further comprises at least one polyarylene other than the kinked rigid-rod polyarylene (P). The polyarylene other than the kinked rigid-rod polyarylene (P) is preferably a kinked rigid-rod polyarylene (P2) of which more than 50 wt. % of the recurring units are recurring units (R2) of one or more formulae consisting of an optionally substituted arylene group, provided said optionally substituted arylene group is linked by each of its two ends to two other optionally substituted arylene groups via a direct C—C linkage, said recurring units (R2) being a mix (M2) consisting of:
from 75 mole % to 100 mole %, based on the total number of moles of the recurring units (R2), of rigid rod-forming arylene units (R2a), said rigid rod-forming arylene units (R2a) being optionally substituted by at least one monovalent substituting group,
with
from 0 to 25 mole %, based on the total number of moles of the recurring units (R2), of kink-forming arylene units (R2b), said kink-forming arylene units (R2b) being optionally substituted by at least one monovalent substituting group.

Unless stated otherwise, the kinked-rigid rod polyarylene (P2) meets advantageously all the characteristics of the kinked-rigid rod polyarylene (P) as above detailed, at any level of preference.

The amount of the recurring units (R2a) and (R2b) of the kinked-rigid rod polyarylene (P2), the number of moles of the kink-forming arylene units (R2b) in the mix (M2), based on the total number of moles of the recurring units (R2), is preferably of at least 1.0%, more preferably at least 5% and still more preferably at least 10%. On the other hand, in the mix (M2), the number of moles of the kink-forming arylene units (R2b), based on the total number of moles of the recurring units (R2), is preferably of at most 20%, and more preferably of at most 18%. Good results are obtained when the polyarylene (P2) is a kinked rigid-rod polyphenylene copolymer, essentially all, if not all, the recurring units of which consist of a mix (M2) of p-phenylene substituted by a phenylketone group with unsubstituted m-phenylene in a mole ratio p-phenylene:m-phenylene of from 80:20 to 95:5, preferably of from 80:20 to 90:10, and still more preferably of about 85:15. Such a kinked rigid-rod polyphenylene copolymer is commercially available from Solvay Advanced Polymers, L.L.C. as PRIMOSPIE™ PR-120 polyphenylene.

In this first particular embodiment, the weight of the polyarylene (P2), based on the total weight of the polymer material (M), may be of at least 1%, at least 5%, of at least 10%, or at least 15%; on the other hand, the weight of the polyarylene (P2), based on the total weight of the material, may be of at most 99%, of at most 95%, of at most 75%, or of at most 60%.

In another particular embodiment, the polymer material (M) further comprises at least one thermoplastic polymer other than a polyarylene, selected from the group consisting of polyamides, polyether block amides, polyimides, polyetherimides, polyamideimides, polyarylethersulfones (such as polyphenylsulfones, bisphenol A polysulfones, polyethersulfones, polyetherethersulfones, polyethersulfoneimides and copolymers and mixtures thereof), polyetherketones, polyetheretherketones, polyetherketoneketones, polyarylene ethers [such as polyphenylene ethers and poly(2,6-dimethyl-1,4-phenylene ether)s], polyphenylene sulfides, polybenzimidazoles, polycarbonates, polyesters, polyurethanes, polyolefins, poly(methyl pentene)s, polytetrafluoroethylenes, polyethylenes, polypropylenes, liquid crystalline polymers, halogenated polymers, and copolymers and mixtures thereof.

In still another particular embodiment, the polymer material (M) further contains at least one fibrous reinforcing agent, in particular an inorganic fibrous reinforcing agent such as glass fiber or carbon fiber, usually in an amount of from 10 to 50 wt. %, based on the total weight of the polymer material (M).

The weight of the optional ingredients, based on the total weight of the material, ranges advantageously from 0 to 75 wt. %, preferably from 0 to 50 wt. %, more preferably from 0 to 25 wt. % and still more preferably from 0 to 10 wt. %, based on the total weight of the polymer material (M). Excellent results are obtained when the material is essentially free, or is even completely free, of said optional ingredients.

The invention claimed is:

1. A medical device ($\Delta$) comprising at least one part ($\pi$) consisting of a polymer material (M) comprising at least one kinked rigid-rod polyarylene (P) of which more than 50 wt. % of the recurring units are recurring units (R) of one or more formulae consisting of an optionally substituted arylene group, provided said optionally substituted arylene group is linked by each of its two ends to two other optionally substituted arylene groups via a direct C—C linkage, said recurring units (R) being a mix ($\mu$) consisting of:
between 0 and 75 mole %, based on the total number of moles of the recurring units (R), of rigid rod-forming arylene units (Ra), said rigid rod-forming arylene units (Ra) being optionally substituted by at least one monovalent substituting group,
with
between 25 and 100 mole %, based on the total number of moles of the recurring units (R), of kink-forming arylene units (Rb), said kink-forming arylene units (Rb) being optionally substituted by at least one monovalent substituting group.

2. The medical device according to claim 1, wherein the recurring units (R) of the kinked rigid-rod polyarylene (P) are a mix (p) consisting of:

between 0 and 75 mole %, based on the total number of moles of recurring units (R), of rigid rod-forming arylene units (Ra) chosen from p-phenylenes optionally substituted by at least one monovalent substituting group, with between 25 and 100 mole %, based on the total number of moles of recurring units (R), of kink-forming arylene units (Rb) chosen from (i) m-phenylenes optionally substituted by at least one monovalent substituting group and (ii) mixes of m-phenylenes with o-phenylenes, wherein both m-phenylenes and o-phenylenes are, independently from each other, optionally substituted by at least one monovalent substituting group.

3. The medical device according to claim 1, wherein the rigid rod-forming arylene units (Ra) of the mix (µ) are p-phenylenes substituted by a phenylketone group.

4. The medical device according to claim 1, wherein the kink-forming arylene units (Rb) of the mix (µ) are unsubstituted m-phenylenes.

5. The medical device according to claim 1, wherein, in the mix (µ), the number of moles of the kink-forming arylene units (Rb), based on the total number of moles of the recurring units (R), is of at least 40%.

6. The medical device according to claim 1, wherein, in the mix (µ), the number of moles of the kink-forming arylene units (Rb), based on the total number of moles of the recurring units (R), is of at most 65%.

7. The medical device according to claim 1, wherein the kinked rigid-rod polyarylene (P) is a kinked rigid-rod polyphenylene, essentially all the recurring units of which consist of a mix of p-phenylene substituted by a phenylketone group with unsubstituted m-phenylene in a mole ratio p-phenylene:m-phenylene of from 45:55 to 55:45.

8. The medical device according to claim 1, wherein it is an orthodontic appliance.

9. A part (π) of a medical device (Δ), said part (π) consisting of a polymer material (M) comprising at least one kinked rigid-rod polyarylene (P) of which more than 50 wt. % of the recurring units are recurring units (R) of one or more formulae consisting of an optionally substituted arylene group, provided said optionally substituted arylene group is linked by each of its two ends to two other optionally substituted arylene groups via a direct C—C linkage, said recurring units (R) being a mix (µ) consisting of:

between 0 and 75 mole %, based on the total number of moles of the recurring units (R), of rigid rod-forming arylene units (Ra), said rigid rod-forming arylene units (Ra) being optionally substituted by at least one monovalent substituting group, with between 25 and 100 mole %, based on the total number of moles of the recurring units (R), of kink-forming arylene units (Rb), said kink-forming arylene units (Rb) being optionally substituted by at least one monovalent substituting group.

10. The part according to claim 9, wherein the recurring units (R) of the kinked rigid-rod polyarylene (P) are a mix (µ) consisting of:

between 0 and 75 mole %, based on the total number of moles of recurring units (R), of rigid rod-forming arylene units (Ra) chosen from p-phenylenes optionally substituted by at least one monovalent substituting group, with between 25 and 100 mole %, based on the total number of moles of recurring units (R), of kink-forming arylene units (Rb) chosen from (i) m-phenylenes optionally substituted by at least one monovalent substituting group and (ii) mixes of m-phenylenes with o-phenylenes, wherein both m-phenylenes and o-phenylenes are, independently from each other, optionally substituted by at least one monovalent substituting group.

11. The part according to claim 9, wherein the rigid rod-forming arylene units (Ra) of the mix (µ) are p-phenylenes substituted by a phenylketone group.

12. The part according to claim 9, wherein the kink-forming arylene units (Rb) of the mix (s) are unsubstituted m-phenylenes.

13. The part according to claim 9, wherein, in the mix (µ), the number of moles of the kink-forming arylene units (Rb), based on the total number of moles of the recurring units (R), is of at least 40%.

14. The part according to claim 9, wherein, in the mix (µ), the number of moles of the kink-forming arylene units (Rb), based on the total number of moles of the recurring units (R), is of at most 65%.

15. The part according to claim 9, wherein the kinked rigid-rod polyarylene (P) is a kinked rigid-rod polyphenylene, essentially all the recurring units of which consist of a mix of p-phenylene substituted by a phenylketone group with unsubstituted in-phenylene in a mole ratio p-phenylene:m-phenylene of from 45:55 to 55:45.

16. The part according to claim 9, wherein said part is an orthodontic component.

17. The part according to claim 16, wherein the orthodontic component is selected from the group consisting of orthodontic brackets and orthodontic wires.

18. A method for the manufacture of the medical device (Δ) according to claim 1, wherein the polymer material (M) is shaped into the part (π) by a melt-processing technique.

19. The method according to claim 18, wherein the melt-processing technique is extrusion.

20. The method according to claim 18, wherein the melt-processing technique is injection-molding.

21. A method for the manufacture of the part (π) of a medical device (Δ) according to claim 9, wherein the polymer material (M) is shaped into the part (π) by a melt-processing technique.

22. The method according to claim 21, wherein the melt-processing technique is extrusion.

23. The method according to claim 21, wherein the melt-processing technique is injection-molding.

24. A method for therapeutically treating a human or animal patient, wherein the method comprises using the medical device (Δ) according to claim 1.

25. A method for surgically treating a human or animal patient, wherein the method comprises using the medical device (Δ) according to claim 1.

26. A method for diagnosing a human or animal patient, wherein the method comprises using the medical device (Δ) according to claim 1.

* * * * *

UNITED STATES PATENT AND TRADEMARK OFFICE
CERTIFICATE OF CORRECTION

| | | |
|---|---|---|
| PATENT NO. | : 8,119,764 B2 | |
| APPLICATION NO. | : 12/206825 | |
| DATED | : February 21, 2012 | |
| INVENTOR(S) | : Maljkovic et al. | |

It is certified that error appears in the above-identified patent and that said Letters Patent is hereby corrected as shown below:

Column 28, line 67, "a mix (p) consisting of:" should read --a mix (μ) consisting of:--.

Column 30, line 16, "ing arylene units (Rb) of the mix (s) are unsubstituted m-phe-" should read --ing arylene units (Rb) of the mix (μ) are unsubstituted m-phe- --.

Column 30, line 31 "with unsubstituted in-phenylene in a mole ratio p-phenylene:" should read --with unsubstituted m-phenylene in a mole ratio p-phenylene:--.

Signed and Sealed this
Seventeenth Day of April, 2012

David J. Kappos
*Director of the United States Patent and Trademark Office*